United States Patent
Metzger et al.

(10) Patent No.: US 11,983,777 B1
(45) Date of Patent: May 14, 2024

(54) SYSTEMS AND METHODS FOR RISK FACTOR PREDICTIVE MODELING WITH MODEL EXPLANATIONS

(71) Applicant: Massachusetts Mutual Life Insurance Company, Springfield, MA (US)

(72) Inventors: Stacy Metzger, Springfield, MA (US); Daniel Garant, Springfield, MA (US); Marc Maier, Springfield, MA (US); Hayley Carlotto, Springfield, MA (US)

(73) Assignee: Massachusetts Mutual Life Insurance Company, Springfield, MA (US)

( * ) Notice: Subject to any disclaimer, the term of this patent is extended or adjusted under 35 U.S.C. 154(b) by 41 days.

(21) Appl. No.: 17/387,626

(22) Filed: Jul. 28, 2021

(51) Int. Cl.
*G06Q 40/08* (2012.01)
*G06F 16/25* (2019.01)
(Continued)

(52) U.S. Cl.
CPC ............. *G06Q 40/08* (2013.01); *G06F 16/25* (2019.01); *G06F 40/55* (2020.01); *G06N 5/04* (2013.01);
(Continued)

(58) Field of Classification Search
CPC ....................................................... G06F 40/55
See application file for complete search history.

(56) References Cited

U.S. PATENT DOCUMENTS

| 8,326,657 | B2 * | 12/2012 | Morse | G16H 10/60 |
| | | | | 705/2 |
| 8,793,146 | B2 * | 7/2014 | Bonissone | G06Q 40/08 |
| | | | | 705/4 |

(Continued)

FOREIGN PATENT DOCUMENTS

| CN | 111652302 A | * | 9/2020 |
| TW | 200929051 A | | 7/2009 |

OTHER PUBLICATIONS

Lundberg, Scott M. et al., "A Unified Approach to Interpreting Model Predictions," In Advances in Neural Information Processing Systems, vol. 30, Nov. 25 2017, 10 pages.
(Continued)

*Primary Examiner* — Scott S Trotter
*Assistant Examiner* — William D Newlon
(74) *Attorney, Agent, or Firm* — Foley & Lardner LLP (57) ABSTRACT

An underwriting estimator predictive machine learning model receives as inputs a limited number of details about an applicant, and outputs an immediate underwriting estimate of risk class. A preliminary pre-screening review redirects applicants with one or more screening impairments to a human-in-the-loop quick quote process. Model inputs include estimator inputs data that are pre-selected from the dataset of impairments data after excluding the screening impairments from the dataset of impairments. The underwriting estimator model may incorporate alternative pathways that output individualized underwriting estimates for some applicants and cohort-level marginal distributions for other applicants. Model outputs also include explanation files providing interpretability of underwriting estimates. The explanation files may include additive feature attribution data and rule based natural language explanations. The underwriting estimator predictive model may apply random forest models with smoker and non-smoker components to model inputs.

21 Claims, 6 Drawing Sheets

(51) Int. Cl.

| | | |
|---|---|---|
| G06F 40/55 | (2020.01) | |
| G06N 5/04 | (2023.01) | |
| G06N 20/00 | (2019.01) | |
| G16H 50/20 | (2018.01) | |
| G16H 50/30 | (2018.01) | |
| G16H 10/60 | (2018.01) | |

(52) U.S. Cl.
CPC ............ *G06N 20/00* (2019.01); *G16H 50/20* (2018.01); *G16H 50/30* (2018.01); *G16H 10/60* (2018.01)

(56) References Cited

U.S. PATENT DOCUMENTS

| | | | | |
|---|---|---|---|---|
| 10,679,294 | B1 * | 6/2020 | Lanzrath | G16H 10/40 |
| 11,176,471 | B1 * | 11/2021 | DeCaprio | G06F 18/2115 |
| 11,354,749 | B2 * | 6/2022 | Jiang | G06N 20/10 |
| 11,494,845 | B1 * | 11/2022 | Hummel | G06N 20/00 |
| 2008/0114620 | A1 | 5/2008 | Donnelli | |
| 2011/0040582 | A1 * | 2/2011 | Mullins | G06Q 40/08 705/4 |
| 2015/0287143 | A1 * | 10/2015 | Gabriel | G06Q 40/08 705/4 |
| 2016/0110815 | A1 * | 4/2016 | Dellaripa | G06Q 40/08 705/4 |
| 2020/0250557 | A1 * | 8/2020 | Kishimoto | G06N 5/045 |
| 2020/0285704 | A1 * | 9/2020 | Rajani | G06F 40/30 |
| 2022/0129792 | A1 * | 4/2022 | Nitta | G06N 20/00 |

OTHER PUBLICATIONS

Maier, Marc et al., "Transforming under-writing in the life insurance industry," In Proceedings of the AAAI Conference on Artificial Intelligence, vol. 33, Jul. 17, 2019, pp. 9373-9380 (8 pages).

Snoek, Jasper et al., "Practical Bayesian Optimization of Machine Learning Algorithms," In Advances in Neural Information Processing Systems, vol. 25, Dec. 2012, 9 pages.

* cited by examiner

SYSTEMS AND METHODS FOR RISK FACTOR PREDICTIVE MODELING WITH MODEL EXPLANATIONS

TECHNICAL FIELD

The present disclosure relates generally to predictive modeling.

BACKGROUND

Traditionally, users such as customers and customer representatives have the option of requesting a quick quote, e.g., rough estimate of risk class, by providing a few details about their client over email. This approach is labor-intensive, can be slow, and may not scale effectively. Conventional solutions may apply software algorithms that more quickly and more precisely process requests and provide quotes. But even these conventional software solutions are unable to provide explanations for preliminary decisions based on the underlying algorithms.

SUMMARY

With the advent of machine learning techniques, algorithmic systems can be quite complex. The algorithmic systems do not provide adequate transparency into factors affecting decisions and scoring. While applying machine learning modeling techniques can produce quicker and more precise quotes, it can be very difficult to explain preliminary underwriting decisions in quick quotes to affected customers in a way that these customers can trust the process. Additionally, from a user's standpoint, algorithmic processing can be opaque, e.g., a black box process in which the user enters items of information just to see the computer system produce a result. Understanding the reasons behind model predictions is desirable.

What is needed are systems and methods that generate immediate underwriting estimates based on a limited number of user inputs. Another need is for underwriting estimator predictive models of improved accuracy that provide users with qualitative and quantitative understandings of underwriting estimates output by these models. An additional need is for systems and methods that provide persons affected by underwriting estimates with a specific reason for any adverse decision.

In systems and methods disclosed herein, a server receives as inputs a limited number of details about an applicant input into an underwriting estimator predictive machine learning model. The underwriter estimator model outputs an immediate underwriting estimate of risk class based on the inputs received. The underwriter estimator model may be configured to determine a risk rank representative of a mortality or morbidity risk for an electronic application for the underwriting estimate by inputting the inputs for the applicant in the limited set of risk factor data. The predictive machine learning model may be trained by inputting into the predictive machine learning model a plurality of historical application details records and a plurality of historical underwriting decision records. The underwriter estimator predictive model may apply random forest models with smoker and non-smoker components to model inputs.

The system may classify the electronic application for the underwriting estimate into one of a first risk group and a second risk group based upon a risk rank determined by the predictive machine learning model. The underwriter estimator model may incorporate alternative pathways that output individualized underwriting estimates for some applicants and cohort-level marginal distributions for other applicants. Model outputs also include explanation files providing interpretability of underwriting estimates. The explanation files may include additive feature attribution data and rule-based natural language explanations.

A preliminary pre-screening review may redirect applicants with one or more screening impairments to a human-in-the-loop quick quote process. Model inputs may include estimator inputs data that are pre-selected from a dataset of impairments data after excluding screening impairments from the dataset of impairments.

In one embodiment, a method comprises executing, by the server, a predictive machine learning model configured to determine a risk rank representative of a mortality or morbidity risk for an input of risk factor data for an electronic application, wherein the predictive machine learning model is trained by inputting into the predictive machine learning model a plurality of historical application details records and a plurality of historical underwriting decision records; classifying, by the server, the electronic application for the underwriting estimate into one of a first risk group and a second risk group based upon the risk rank determined by the predictive machine learning model; when the applicant is classified into the first risk group, generating, by the server, an individualized underwriting estimate file for the applicant and a first explanation file including interpretability data for the individualized underwriting estimate file, for display by the user device of information representative of the individualized underwriting estimate file and the first explanation file; and when the applicant is classified into the second risk group, generating, by the server, a cohort-level distributions file for the applicant and a second explanation file including interpretability data for the cohort-level distributions file, for display by the user device of information representative of the cohort-level distributions file and the second explanation file.

In another embodiment, a system comprises an analytical engine server containing a processor configured to execute a plurality of non-transitory computer-readable instructions configured to: execute a predictive machine learning model configured to determine a risk rank representative of a mortality or morbidity risk for an input of risk factor data for an electronic application, wherein the predictive machine learning model is trained by inputting into the predictive machine learning model a plurality of historical application details records and a plurality of historical underwriting decision records; classify the electronic application for the underwriting estimate into one of a first risk group and a second risk group based upon the risk rank determined by the predictive machine learning model; when the applicant is classified into the first risk group, generate an individualized underwriting estimate file for the applicant and a first explanation file including interpretability data for the individualized underwriting estimate file, for display by the user device of information representative of the individualized underwriting estimate file and the first explanation file; and when the applicant is classified into the second risk group, generate a cohort-level distributions file for the applicant and a second explanation file including interpretability data for the cohort-level distributions file, for display by the user device of information representative of the cohort-level distributions file and the second explanation file.

In yet another embodiment, a computer storage medium having computer-executable instructions stored thereon that, when executed by one or more processors, cause the one or more processors to perform operations comprising: executing a predictive machine learning model configured to determine a risk rank representative of a mortality or morbidity risk for an input of risk factor data for an electronic application, wherein the predictive machine learning model is trained by inputting into the predictive machine learning model a plurality of historical application details records and a plurality of historical underwriting decision records; classifying the electronic application for the underwriting estimate into one of a first risk group and a second risk group based upon the risk rank determined by the predictive machine learning model; when the classifying step classifies the applicant into the first risk group, generating an individualized underwriting estimate file for the applicant and a first explanation file including interpretability data for the individualized underwriting estimate file, for display by the user device of information representative of the individualized underwriting estimate file and the first explanation file; and when the classifying step classifies the applicant into the second risk group, generating a cohort-level distributions file for the applicant and a second explanation file including interpretability data for the cohort-level distributions file, for display by the user device of information representative of the cohort-level distributions file and the second explanation file.

Other objects, features, and advantages of the present disclosure will become apparent with reference to the drawings and detailed description of the illustrative embodiments that follow.

BRIEF DESCRIPTION OF THE DRAWINGS

Non-limiting embodiments of the present disclosure are described by way of example with reference to the accompanying figures which are schematic and are not intended to be drawn to scale. Unless indicated as representing the background art, the figures represent aspects of the disclosure.

DETAILED DESCRIPTION

In the following detailed description, reference is made to the accompanying drawings, which depict non-limiting, illustrative embodiments of the present disclosure. Other embodiments may be utilized and logical variations, e.g., structural and/or mechanical, may be implemented without departing from the scope of the present disclosure. To avoid unnecessary detail, certain information, items, or details known to those skilled in the art may be omitted from the following.

An insurance company uses underwriting to determine whether a potential customer is eligible for insurance and what rate that potential customer should pay for the insurance if eligible. The underwriting process assesses a risk class for a customer along with a corresponding premium, and in some instances, may deny coverage for the customer. Some conventional life insurance require an estimate of the expected lifetime of an individual at the time of application, commonly called the "mortality risk." Actuarial algorithms compute the cost of covering mortality risk over the lifetime of the policy and translate it into a set of premium payments required throughout a policy's term. Life insurance risk assessment has primarily consisted of point systems developed by medical doctors and experienced underwriters. Such protocols commonly calculate risk by mapping medical and behavioral attributes to point values that either debit or credit an overall score. A life insurance underwriter reviews an application to calculate the net number of points and to determine one of several risk classes that determine pricing according to aggregate mortality.

Applications for insurance products, such as life insurance applications, can be lengthy both in terms of questions and process. Many applications require lab work (e.g., collection of blood and urine samples) and review of attending physician statements. Clients seeking life insurance coverage often want to quickly estimate likely rates. There are various conventional insurance processes to provide clients and their agents with quick quotes, also referred to herein as "quick quotes." Quick quotes typically take the form of a rate estimate or a risk class estimate. Quick quotes are typically preliminary and subject to change based on more thorough underwriting.

Another option available from some insurance providers is for clients to submit an "informal" application. Informal applications require more details up-front, e.g., typically via unstructured documents such as documented medical history and cover letter. Informal submissions have a longer turnaround time than quick quotes and result in more accurate risk class estimates.

Traditionally, customer representatives such as producers (also advisors, agents) have the option of requesting a quick quote (rough estimate of risk class) by providing a few details about their client using electronic message (e.g., email). This approach is labor-intensive, can be slow and may not scale effectively. Additionally, while applying machine learning modeling techniques to quick quotes can mitigate these concerns, it can be very difficult to explain preliminary underwriting decisions in quick quotes to affected customers in a way that these customers can trust the process. Understanding the reasons behind model predictions is quite important in assessing trust. Trust in individual model predictions is fundamental if one is affected by the model predictions.

To mitigate these concerns, the systems and methods of the present disclosure employ a predictive machine learning model to produce quick quotes for life insurance and similar risk-pooling products. The embodiments herein recite an underwriting estimator predictive model and may refer to a model prediction as an underwriting estimate. The predictive model receives as input a limited number of details about a prospective client, and outputs a rough estimate of risk class. Upon receiving an application for underwriting estimation and required inputs, the predictive model generates an immediate underwriting estimate for digital delivery to a user.

The system and method of the present disclosure apply machine learning methods to underwriting estimation. The predictive model may include random forest models to predict risk class assignments. For example, in order to avoid assigning a smoker to a non-tobacco risk class and to avoid assigning a non-smoker to a tobacco risk class, predictive modeling fits two models. A smoker model targets cases with a set of final risk classes having tobacco status, and a non-smoker model targets cases with a set of final risk classes having non-tobacco status.

Model training data sources may include a historical application details dataset and a historical underwriting decisions dataset. Training data may include cases submitted during historical time frame, e.g., a time period through current data. In an embodiment, the dataset is limited to cases receiving underwriting decisions, e.g., no incomplete cases.

In an embodiment, the underwriting estimator predictive model reduces the need for human-in-the-loop quick quoting, while deferring to underwriter review in certain situations. For example, the underwriting estimator predictive model may defer to underwriter review in situations involving applicants with certain medical conditions or applications having face amounts exceeding a predefined threshold. In an embodiment, systems and methods of the present disclosure may integrate the underwriting estimator predictive model into an application workflow in which the user may be directed to contact an underwriter in certain situations and may receive a model-based quote in other situations. In various embodiments, in conjunction with model-based quotes embody interpretability information or model explanations, which explain preliminary underwriting decisions in underwriting estimates to affected users.

In an embodiment, the underwriting estimator predictive model incorporates alternative pathways for generating a model-based quote depending on situation of a prospective client or prospective product sale. In some pre-determined situations, the predictive model may present information concerning cohort-level marginal distributions and defer to alternative underwriting processes for a more intensive review. In other pre-determined situations, the predictive model may present a more refined individual-level risk class estimate and may present that individual estimate in the context of cohort-level information. In an embodiment, in determining cohort-level marginal distributions, the present disclosure refers to a cohort as a five-year age band, gender, and smoking status.

In various embodiments, at the time of generating a model-based underwriting estimate prediction for display to a user, the underwriting estimator generates an explanation file including real-time interpretability data for the underwriting estimate prediction. As used in the present disclosure, "explanations" may be textual and visual artifacts that provide users such as producers and consumers with understanding of underwriting estimator machine learning model predictions. An explanation may provide an understanding of an individual prediction of an underwriting estimator model. An explanation may provide an understanding of information concerning cohort-level marginal distribution output by the underwriting estimator model. The explanation may provide an understanding of the underwriting estimator machine learning model itself. A machine learning model can provide quantitative predictions, and the explanation can provides one or both of qualitative understanding and quantitative understanding of the model's quantitative predictions. Explanations of machine learning models are commonly associated with "interpretability." As used herein, "interpretability" denotes the degree to which a human can understand the cause of a decision by a machine learning model.

As used in the present disclosure, an explanation model, also herein called an interpretability model, treats explanations of predictions of a machine learning model as a model itself. In various embodiments, an explanation model implements additive feature attribution for interpretability of underwriting estimator outcomes. Additive feature attribution provides various desirable properties in an explanation method. In various embodiments, an explanation model using additive feature explanation provides users with real-time explanations of underwriting estimator predictions.

Present system and methods estimate a risk class that users can translate into a rate. In an illustrative framework, risk classes for life underwriting include, in increasing order of risk:

1. Ultra preferred non-tobacco (UPNT)
2. Select preferred non-tobacco (SPNT)
3. Standard non-tobacco (NT)
4. Sub-standard non-tobacco
5. Select preferred tobacco (SPT)
6. Standard tobacco (T)
7. Sub-standard tobacco In the present disclosure, "preferred eligibility" may refer to a risk rank that might be assigned one of the preferred risk classes UPNT, SPNT, or SPT.

As used in the present disclosure, an "impairment" may refer to a variable associated with a health outcome or state, such as a risk of disease, infection and/or health-related event, e.g., a stroke, diabetes, heart attack, cancer and death. In the present disclosure, impairments may be sometimes called risk factors. Impairment may be correlated with a health outcome or state and may have a causal relationship with the health outcome or state. Examples of impairments include HIV and AIDS; sexually transmitted diseases (STD); cholesterol, (including LDL and HDL) and triglycerides (e.g., as indicators of heart disease risk factors); hemoglobin A1C, fructosamine and glucose levels (e.g., as indicators of diabetes); creatinine, hemoglobin and proteins (e.g., as indicators of kidney disease); and urine acidity (e.g., as indicator of impaired kidney function or diabetes). Impairments may be measured using clinical assessments based on collected blood and urine samples, typically by testing the collected fluids to screen for numerous indicators of diseases and conditions. Typical medical examinations also screen for nicotine and cotinine in the urinalysis in order to determine tobacco usage. Additionally, impairments may be obtained from other sources such as self-reporting by applicants. The underwriting estimator predictive modeling may tie various impairments to all-cause mortality or morbidity predictions and to specific causes of mortality or morbidity.

Figure 1:
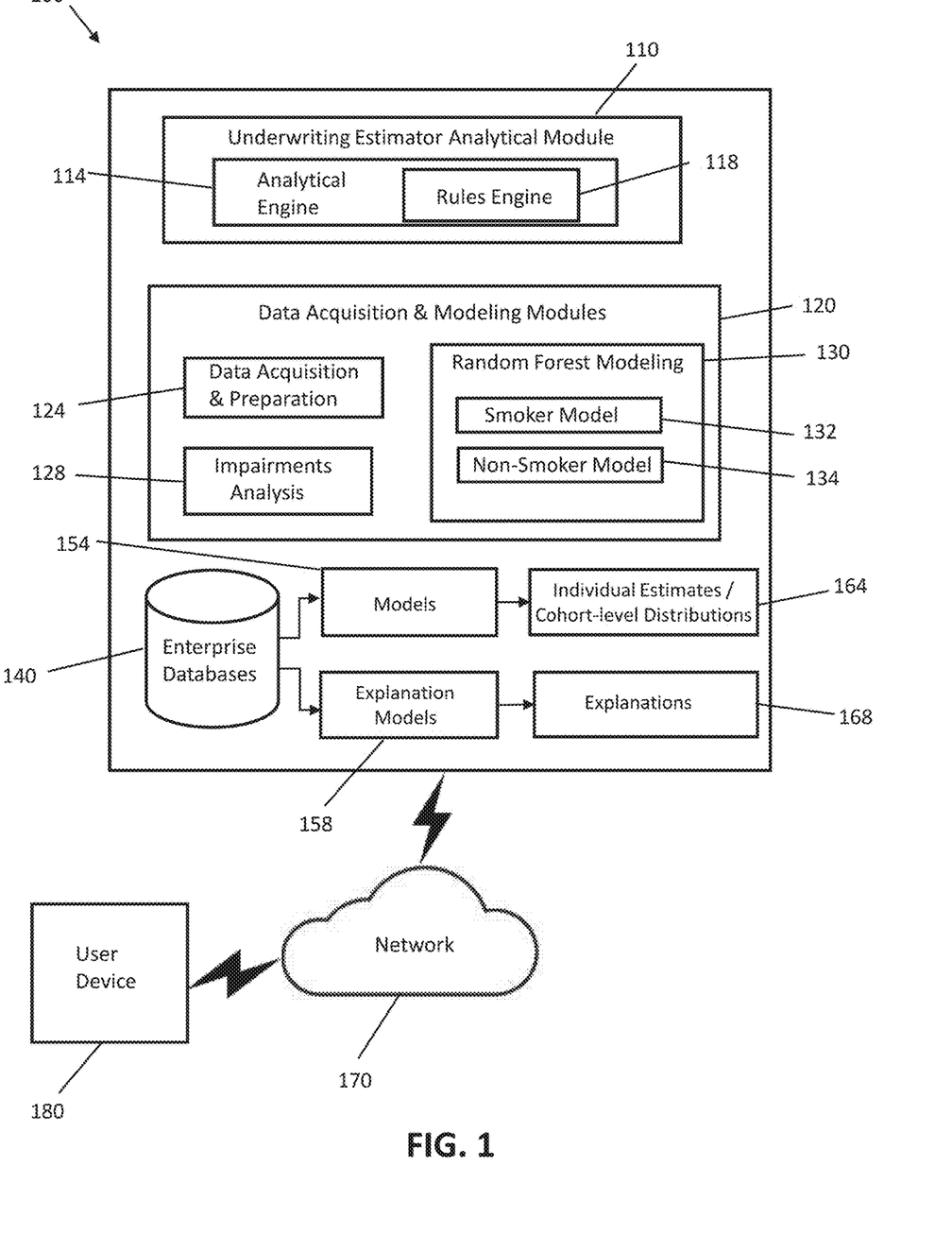
FIG. 1 is a system architecture for an underwriting estimator system including an explanation model, according to an embodiment.

FIG. 1 shows a system architecture for an underwriting estimator system 100. The underwriting estimator system 100 may be hosted on one or more computers (or servers), and the one or more computers may include or be communicatively coupled to one or more databases. The underwriting estimator system 100 may employ predictive modeling to produce quick quotes for life insurance and other risk-pooling products such as disability insurance. The system 100 receives a limited number of inputs about an applicant, and outputs a rough estimate of risk class.

A sponsoring enterprise for underwriting estimator system 100 can be an insurance company or other financial services company, which may be represented by insurance agents or advisors. In some cases, an insurance agent may be associated with only a single insurance provider (sometimes referred to as a "captive" insurance agent). In other cases, an "independent" insurance agent, sometimes called an "insurance broker," may be associated with several different insurance providers. A user (e.g., customer or insurance agent) can submit an application for quick quote via user device 180 and may receive an immediate underwriting estimate with an explanation of underwriting estimator model predictions.

Underwriting estimator analytical module 110 includes an analytical engine 114 and a rules engine submodule 118. The rules engine submodule 118 may execute thousands of automated rules encompassing health, behavioral, and financial attributes stored in enterprise databases 140. As used herein, a module may represent functionality (or at least a part of the functionality) performed by a server and/or a processor. For instance, different modules may represent different portion of the code executed by the analytical engine server to achieve the results described herein. Therefore, a single server may perform the functionality described as being performed by separate modules.

Analytical engine 114 can be executed by a server, one or more server computers, authorized client computing devices, smartphones, desktop computers, laptop computers, tablet computers, PDAs and other types of processor-controlled devices that receive, process, and/or transmit digital data. Analytical engine 114 can be implemented using a single-processor system including one processor, or a multi-processor system including any number of suitable processors that may be employed to provide for parallel and/or sequential execution of one or more portions of the techniques described herein. Analytical engine 114 performs these operations as a result of central processing unit executing software instructions contained within a computer-readable medium, such as within memory. In one embodiment, the software instructions of the system are read into memory associated with the analytical engine 114 from another memory location, such as from a storage device, or from another computing device via communication interface. In this embodiment, the software instructions contained within memory instruct the analytical engine 114 to perform processes described below. Alternatively, hardwired circuitry may be used in place of, or in combination with, software instructions to implement the processes described herein. Thus, implementations described herein are not limited to any specific combinations of hardware circuitry and software.

In various embodiments, predictive models 154 apply machine learning predictive modeling to enterprise data 140 to derive model predictions 164. In various embodiments, model predictions 164 include individual estimates and cohort-level distributions. In various embodiments, model predictions 164 include risk scoring information, also herein called risk ranks. Risk ranks may include, for example, quantitative rates that can be used to generate rate estimate, and risk classes that can be used to generate risk class estimates. In an example, risk ranks include the user's percentile within the score distribution for a population of similar users. Risk ranks can define one or more bins as percentile ranges in a percentile distribution for a population of general users. Risk ranks can rank cases by the likelihood of belonging to one risk class or the other. Risk ranks may determine a quantitative risk score, such as net number of points, for the user and translate this risk score into one of several coarse-grained risk classes. Risk ranks can include a risk class to which the user has been assigned.

In parallel with predictive modeling of underwriting, an explanation model 158, also herein called interpretability model, generates explanations 168 of model outcomes. Explanation model 158 can generate an explanation file for display on user device 180. An explanation file displayed by user device can include interpretability data based on predictive machine learning modeling by predictive models 154. For example, the displayed explanation file can include quantitative or qualitative risk ranks and natural language explanations of an underwriting estimator prediction 164.

Data acquisition and preparation module 124 applies data preparation procedures to the historical application details and historical underwriting decisions to yield an extensive data set with engineered features having improved predictive values. In an example, data acquisition and preparation 124 module prepared a dataset consisting of applications submitted from 2017 through current date and receiving underwriting decisions (no incomplete cases). Predictive models 154 were then trained by application of models within random forest modeling ensemble 130.

In various embodiments, some applicants are not eligible for quick quoting via predictive model 154. The underwriting estimate predictive model may be available for applicants satisfying prerequisites for various parameters. In an example, eligibility requirements include prerequisites for available product types (e.g., whole life insurance, term life insurance); face amounts (e.g., face amounts within a first range for whole life, and within a second range for term life); and applicant age (e.g., age between upper and lower limits). Applicants that fail to meet these requirements may be directed to an existing human-in-the-loop process. In addition, the predictive model may exclude applicants that have serious medical conditions or impairments that almost invariably lead to substandard ratings or declined coverage. To support this goal, impairments analysis module 128 contains data on screening impairments and input impairments. In the present disclosure, screening impairments, also called pre-screening impairments or screening impairments data, may refer to impairments that if present would knock an applicant out of model-based quoting during a preliminary, pre-screening phase of an application. Estimator input impairments, also herein called estimator input impairments data, refer to impairments that are used as inputs within predictive models 154. In an embodiment, based on predictive modelling applied to estimator input impairments for a given applicant, predictive models 154 may determine that an applicant is only eligible to receive cohort-based underwriting estimates 164, not individual underwriting estimates 164.

In various embodiments, underwriting estimator system 100 transmits reports of model outcomes 164, such as underwriting estimates including individual estimates and cohort-level distributions, to user device 180 via network 170. Interpretable underwriting system 100 also may transmit explanations 168 of model outcomes to user device 180. Users associated with a user device 180 may include customers (e.g., applicants for insurance) and other users such as insurance agents, underwriters, system developers or other representatives of an insurance company, other financial services company, or insurance broker, among other possibilities. Underwriting estimates system 100 may generate immediate underwriting estimator predictions 164 and explanations 168.

Figure 2:
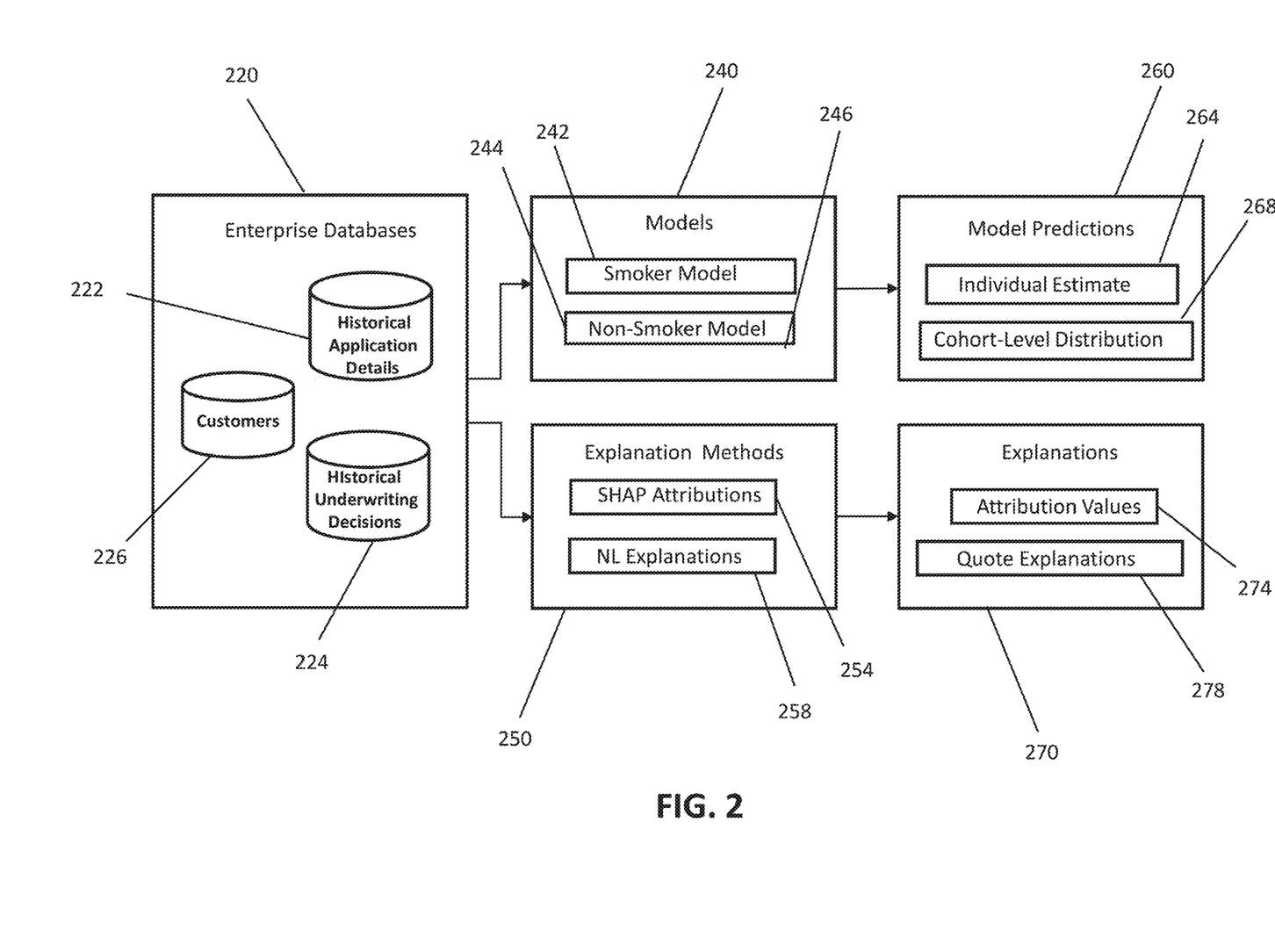
FIG. 2 is a schematic diagram of databases, models, and model outputs of a machine learning underwriting estimator system with explanations, according to an embodiment.

In the underwriting estimator system 200 of FIG. 2, enterprise databases 220 include various databases that may be under custody of a sponsoring enterprise, including historical application details database 222, historical underwriting decisions database 224, and customer database 226. Enterprise databases 220 are organized collections of data, stored in non-transitory machine-readable storage. The databases may execute or may be managed by database management systems (DBMS), which may be computer software applications that interact with users, other applications, and the database itself, to capture (e.g., store data, update data) and analyze data (e.g., query data, execute data analysis algorithms). In some cases, the DBMS may execute or facilitate the definition, creation, querying, updating, and/or administration of databases. The databases may conform to a well-known structural representational model, such as relational databases, object-oriented databases, and network databases. Example database management systems include MySQL, PostgreSQL, SQLite, Microsoft SQL Server, Microsoft Access, Oracle, SAP, dBASE, FoxPro, IBM DB2, LibreOffice Base, FileMaker Pro. Example database management systems also include NoSQL databases, e.g., non-relational or distributed databases that encompass various categories: key-value stores, document databases, wide-column databases, and graph databases.

An ensemble of random forest models 240 includes smoker model 242 and non-smoker model 244. In an example, predictive models 240 were random forest models trained against a large corpus of historical underwriting applications details 222 and historical underwriting decisions 224 of a sponsoring enterprise. In parallel with predictive modeling of underwriting, explanation methods 250, also herein called "explanation models" or "interpretability models," generate explanations 270 of model outcomes. Example methods 250 include SHAP (SHapley Additive exPlanation) explanations 254, which generate attribution values 274 that provide quantitative explanations of model outcomes, and natural language (NL) explanations 258, which generate text explanations 278 of quotes.

SHAP explanations 254 incorporate additive feature attribution. Additive feature attributions describes the sensitivity of models 240 to different values in a rigorous manner. An example additive feature attributions module employs a SHAP values (SHapley Additive exPlanation) algorithm. The additive feature attribution module can execute a Kernel SHAP algorithm. The additive feature attribution module can execute a Tree SHAP algorithm. Additive feature attributions can generate explanations of various outputs of random forest survival models 240, including for example explanations of raw output of the tree model, output of the model transformed into probability space, and model performance metrics broken down by feature.

Figure 5:
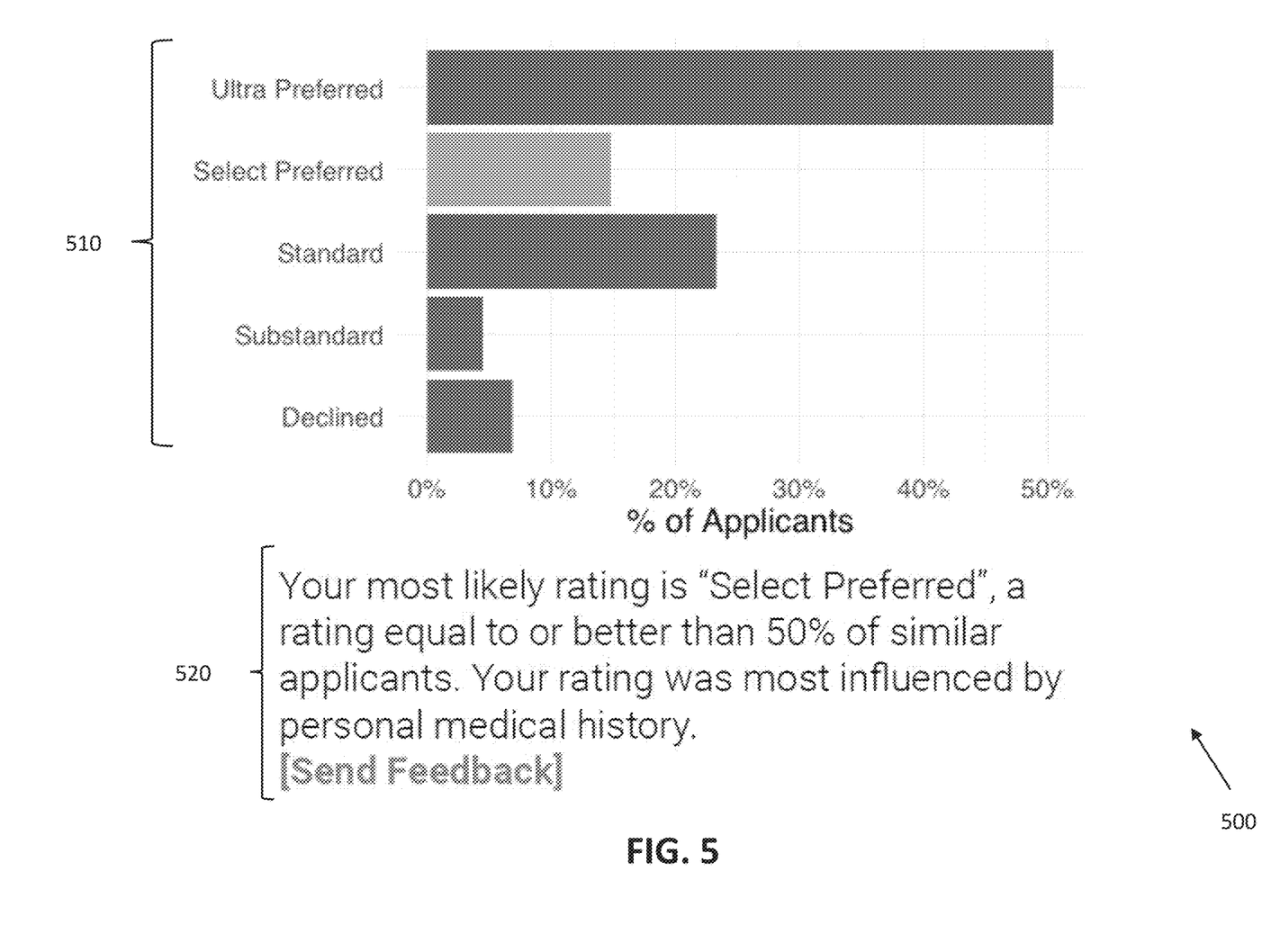
FIG. 5 displays an individualized underwriting estimate with explanation of a machine learning underwriting estimator model prediction, according to an embodiment.
Figure 6:
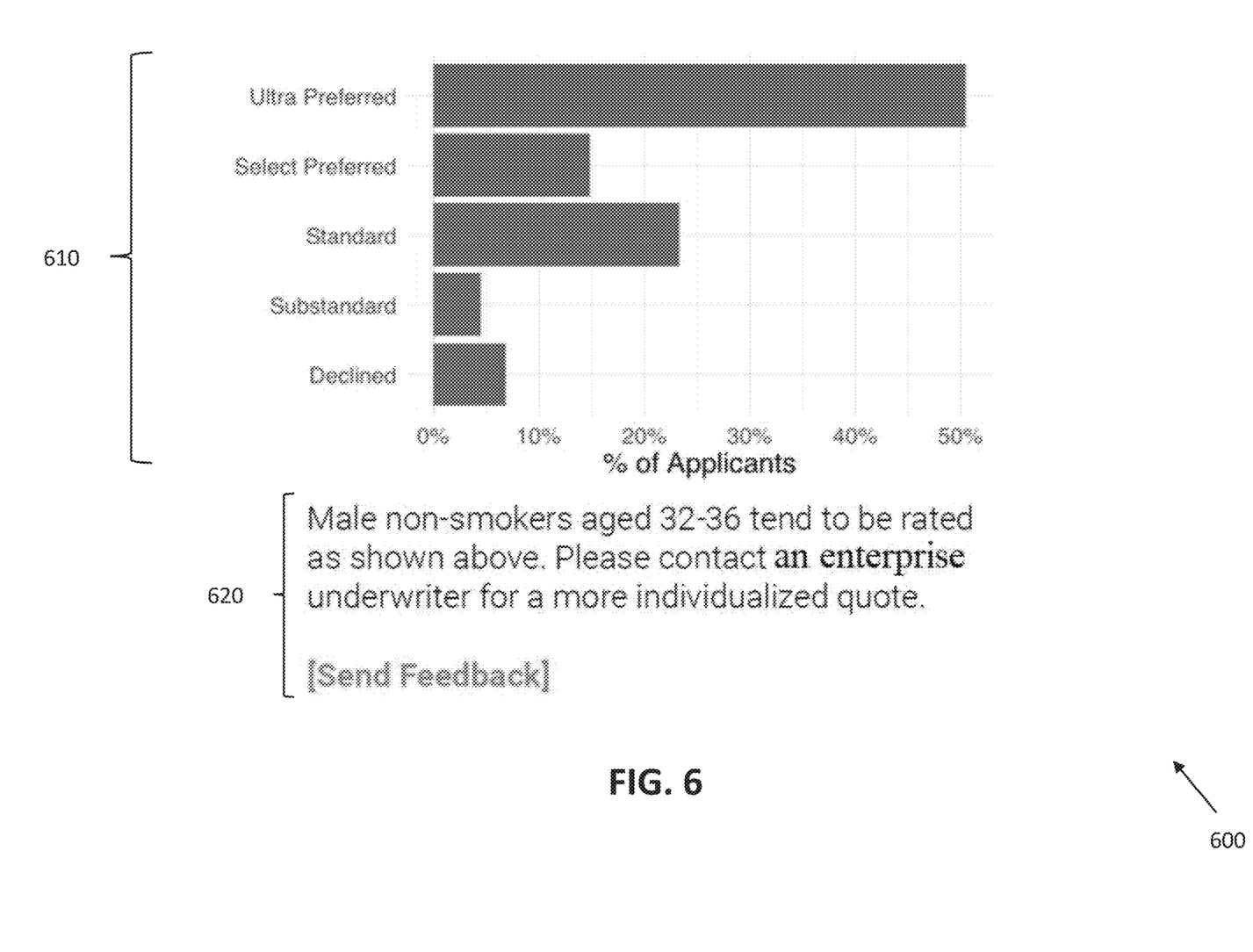
FIG. 6 displays a cohort level estimate with explanation of a machine learning underwriting estimator model prediction, according to an embodiment.

Explanations can include either or both text data and graphical data determined by explanation module 250. In an embodiment, natural language explanations 258 may be a rule-based natural language component of explanation methods 250 that translates model predictions 260 into standardized text explanations. Text explanations can describe individual underwriting estimates 264 and cohort-level underwriting estimates 268. Explanations can include qualitative information and quantitative information about underwriting estimates. FIGS. 5 and 6 show examples of natural language explanations accompanying graphical depictions of underwriting estimates.

Figure 3:
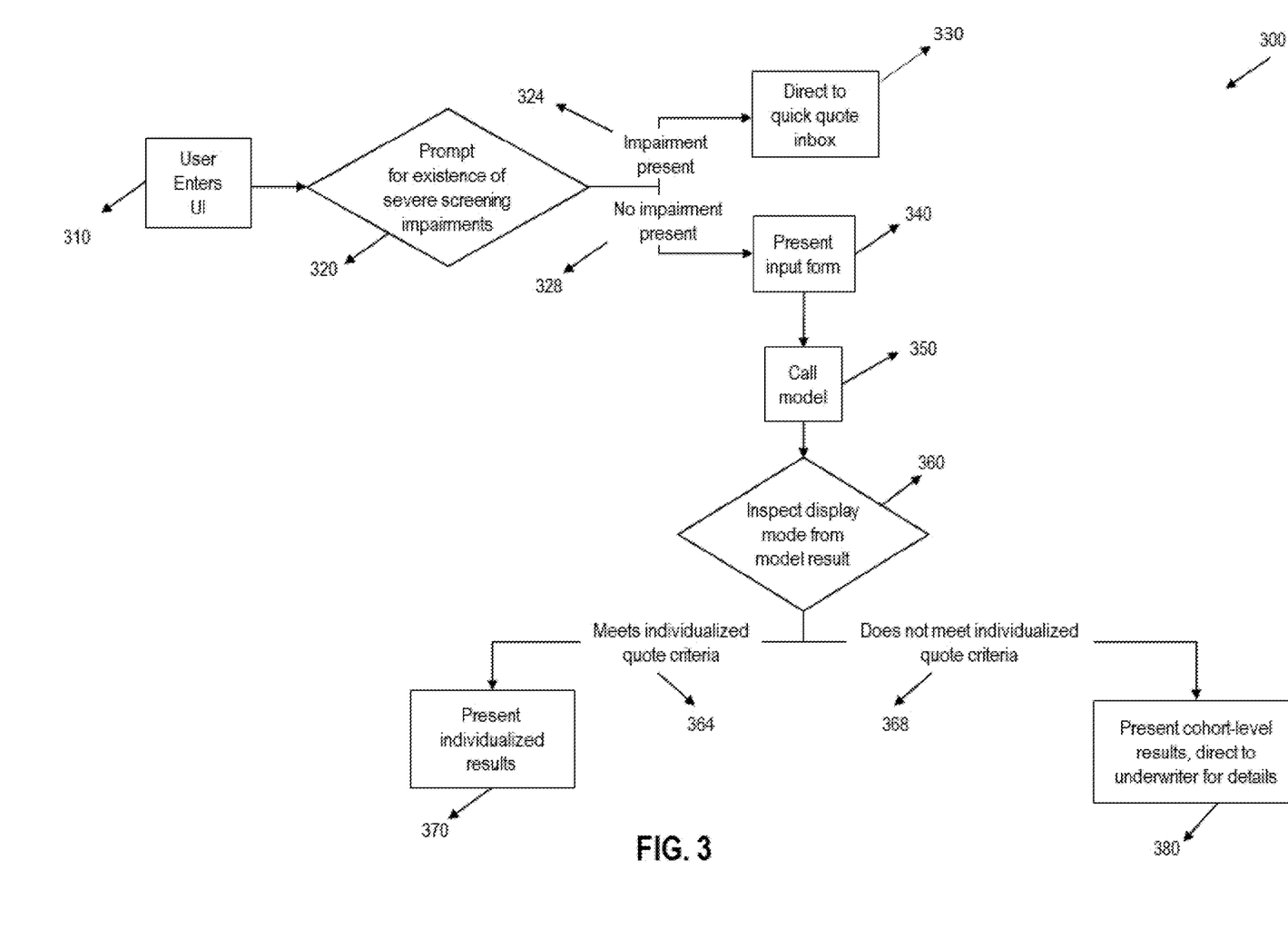
FIG. 3 illustrates a flow chart diagram for a workflow, according to an embodiment.

FIG. 3 is a flow chart diagram of a processor-based workflow of an application for quick quote 300. At 310, a user such as an insurance agent, producer, or consumer (e.g., applicant for insurance) enters the user interface (UI) of the application for quick quote. In an embodiment, the system has a web facing portal with a UI configured to receive inputs and display outputs. To pre-screen for severe impairments without burdening the interface with many inputs, the UI prompts the user up-front to indicate if the applicant experiences any one of a list of screening impairments, i.e., particularly severe impairments. The system may route the inputted application to a human-in-the-loop quick quoting process if one or more screening impairment is present. At step 320, the UI prompts the user to report existence of screening impairments. At step 320 the UI may prompt the user to enter other parameters to determine whether the applicant satisfies other eligibility criteria for receiving an underwriting estimate, such as criteria based on product type, face amount, and applicant age.

In an embodiment, to determine what impairments are screening impairments, model training analyzes impairments data in historical applicant details 222 and historical underwriting decisions 224 to calculate the frequency with which each impairment is associated with a substandard rating, or with a decision to decline underwriting. In an example, using a dataset of ~200,000 cases across 111 impairments meeting the criteria listed above, impairments analysis 128 identified a set of screening impairments with substandard/decline rate of 50% or more. Applicants with these screening impairments may be directed to human-in-the-loop quoting 330, and these screening impairments were excluded from the model's training set (estimator input impairments). In an embodiment, the screening impairments are pre-selected from a dataset of impairments data by determining impairments data with highest risk ranks.

If the processor determines 324 that an applicant has one or more screening impairments or other disqualifying criteria, the UI directs the user to a quick quote input form or other human-in-the-loop process 330, and the workflow ends. If the processor determines 328 that an applicant does not have screening impairments, the UI displays 340 an input form to receive user inputs. In an embodiment, the user input form presents a limited number of inputs corresponding to a pre-determined set of risk factor data. In the present disclosure, risk factor data may include impairments. The model may tie risk factor data to all-cause mortality or morbidity predictions and to specific causes of mortality or morbidity. In various embodiments, risk factor data include estimator input impairments. In an embodiment, the estimator input impairments are pre-selected from a dataset of impairments data by excluding the screening impairments and determining remaining impairments with highest risk ranks.

After receiving user inputs at 340, the processor calls the model at 350 and applies the model to user inputs received (e.g., risk factor data). At 360 the processor inspects the model result to determine an output format for display of model predictions. In an embodiment, at step 360 the processor determines a risk rank representative of a mortality or morbidity risk for the electronic application and classifies the application into one of a first risk group and a second risk group based upon the risk rank determined.

If the processor determines 364 that model results meet individualized quote criteria, the processor presents individualized results for display at 370. If the processor determines 368 that model results do not meet individualized quote criteria, the processor presents cohort-level results for display at 380. In an embodiment, at steps 360, 364 the processor determines a risk rank representative of a mortality or morbidity risk for the application and classifies the application into a first risk group. In an embodiment, at steps 360, 368 the processor determines a risk rank representative of a mortality or morbidity risk for the application and classifies the application into a second risk group.

In various embodiments of steps 370, 380, the processor presents explanations of model predictions for display in conjunction with model predictions. In an example, the processor presents cohort-level results 380 for display in conjunction with an explanation directing the user to an underwriter for details.

In an example, after excluding particularly severe impairments (screening impairments) from the model training set, model training employed dataset of ~200,000 cases and 87 impairments. Of the remaining impairments, impairments analysis identified model inputs that would be effective in distinguishing among standard and preferred classes. Estimator input impairments were organized into a two-level hierarchy in designing model inputs logic. Level 1 impairments (e.g., blood disorder) capture a large group of medical conditions. In many cases, level 1 impairments require responding to more detailed (level 2) questions. Level 2 impairments (e.g., anemia) correspond to these more specific medical conditions. Level 2 impairments typically provide an appropriate level of specificity for an application, because several level 1 impairments (e.g., heart condition, endocrine disorder) have predominantly level 2 medical risk factors (hypertension and diabetes, respectively). In an example, model training determined which impairments may be most valuable to include as inputs to the risk class model by assessing the impact of each impairment on risk class assignments and the number of applicants disclosing that impairment. Impairments analysis calculated the product of the number of cases rated standard, and the number of cases in which the impairment was self-disclosed.

In an example of estimator input impairments corresponding to top-scored impairments after excluding screening impairments, only the five top-scored impairments were included as estimator input impairments to keep the number of inputs small. These input impairments included hypertension, asthma, hypothyroidism, diabetes, and hyperlipidemia. In practice, each of these impairments may be disclosed during the underwriting estimator application process, or may be discovered during subsequent underwriting.

A general list of model inputs and data sources may include:
- Age, binned into roughly 5-year bands: [17, 22.5), [22.5, 27.5), [27.5, 32.5), etc. based on application data. This 5-year band representation prevents over-fitting to limited data for specific ages.
- BMI, treated as a continuous input, with preference given to height & weight reported on the lab slip if available, otherwise based on application data. Cases with a BMI under 10 or over 55 are excluded as outliers.
- Tobacco use, based on final underwriting assignment and applicant self-disclosure of smoking 13-24 months ago, which renders a non-smoker case non-preferred eligible.
- Gender, based on application data.
- Hypertension, based on blood pressure readings from labs, and represented ordinally in accordance with American Heart Association guidance.
  - Normal: Systolic<120 and Diastolic<80
  - Elevated: 120≥Systolic≤129 and Diastolic<80
  - Hypertension Stage 1: 120≥Systolic≤129 and 50≥Diastolic≤89
  - Other (abnormal/stage II hypertension)
- Asthma, based on application self-disclosure or discovered and annotated by underwriter in Medical Information Bureau (MIB) submission.
- Hypothyroidism, based on application self-disclosure or MIB code.
- Diabetes, based on application self-disclosure or MIB code.
- Hyperlipidemia, based on readings from labs represented ordinally.
  - Good: Total cholesterol≤200
  - Borderline: 200≥Total cholesterol≤239
  - High: Total cholesterol≥240

In various embodiments, underwriting estimator models 240 comprise machine learning models that are trained on various sets of training data. Suitable machine learning model classes include but are not limited to random forests, logistic regression methods, support vector machines, gradient tree boosting methods, nearest neighbor methods, and Bayesian regression methods. Using the inputs described above, model training developed random forest models to predict risk class assignments. Other models were considered in addition to random forests, including gradient boosting and multi-class logistic regression. Random forests provided strongest performance.

Smoking status imposes hard constraints on risk class assignments as a smoker cannot be assigned a non-tobacco risk class and vice-versa. To handle this constraint, model development fit two models. In an example, a smoker model targeted cases with a final risk classes of T, SPT, and substandard/decline with tobacco status (~12,000 cases). A non-smoker model targeted cases with a final risk class of UPNT, SPNT, NT, and substandard/decline with non-tobacco status (~180,000 cases). In both cases, substandard/decline was treated as one class. These models were implemented very similarly, one exception being that the non-smoker model includes an additional input indicating tobacco use within 13-24 months. This would be considered a non-tobacco case, but affects preferred eligibility. Hyperparameters were tuned separately for each model, given the dramatic difference in sample size.

One modeling challenge is that applicants will not always have detailed information about their blood pressure and cholesterol. For instance, applicants may know that they have "high blood pressure," but may not know whether their blood pressure would be classified as elevated, stage I hypertension, or stage II hypertension. Model development referred to "high blood pressure" as a coarse input, and stage II hypertension as a refined input. In an example, a UI prompts the user for coarse inputs (high BP/cholesterol), and provides the option of entering refined values. Model development fitted models on refined inputs, and employed a marginalization procedure to produce an underwriting estimate. This procedure developed distributions of refined input values, conditioned on 10-year age band and obesity (BMI>30), and used these distributions to marginalize over any case in which model inputs include only coarse indications.

TABLE 1

| | | Cholesterol | | Blood Pressure | | HTN Stage |
|---|---|---|---|---|---|---|
| Build | Age Band | Borderline | High | Elevated | HTN Stage I | II/Other |
| Not Obese | [15, 25) | 81.7% | 18.3% | 54.0% | 42.8% | 3.2% |
| Not Obese | [25, 35) | 76.3% | 23.7% | 46.5% | 48.3% | 5.2% |
| Not Obese | [35, 45) | 76.4% | 23.6% | 41.7% | 51.9% | 6.5% |
| Not Obese | [45, 55) | 74.1% | 25.9% | 38.7% | 54.5% | 6.8% |
| Not Obese | [55, 65) | 70.2% | 29.8% | 39.1% | 54.0% | 6.8% |
| Obese | [15, 25) | 77.2% | 22.8% | 43.8% | 52.1% | 4.1% |
| Obese | [25, 35) | 72.9% | 27.1% | 36.6% | 57.9% | 5.5% |
| Obese | [35, 45) | 73.5% | 26.5% | 33.3% | 60.4% | 6.3% |
| Obese | [45, 55) | 71.7% | 28.3% | 31.2% | 60.9% | 7.9% |
| Obese | [55, 65) | 72.6% | 27.4% | 31.0% | 60.6% | 8.4% |

The following marginalization procedure was employed, in which conditional distributions were evaluated as shown in Table 1. In the formula below, function f(x,b,c) represents a prediction from the random forest model. This function is a probability simplex over risk classes for inputs x, refined blood pressure b, and refined cholesterol c.

$$\Sigma_b P(b|Age_{10}, Obese) \Sigma_c P(c|Age_{10}, Obese) f(x,b,c)$$

The above formula can be modified if refined values are available for either blood pressure or cholesterol. The procedure then may present the risk class distribution p to the applicant. Alternatively, the procedure may present to the applicant the most likely risk class assignment (arg $\max_r \vec{p}_r$) alongside cohort-level marginal P(class|Age$_5$, Gender). An example output that presents the most likely risk class assignment alongside cohort-level marginal is shown in FIG. 5.

In an embodiment, applicants with a BMI greater than or equal to 35 are not preferred eligible and applicants with a BMI greater than or equal to 38 receive a sub-standard risk class. These risk rank rules may be enacted by suppressing the probability estimates for the appropriate classes (e.g., $\vec{p}_{UPNT} \leftarrow$, $\vec{p}_{SPNT} \leftarrow 0$), and renormalizing $\vec{p}$.

To control complexity of random forest models, model training tuned a parameter governing the minimum number of samples allowed in a leaf node. Larger values yield shallower and less complex trees. This parameter was tuned separately for the smoker and non-smoker models, using five-fold cross validation with cross-entropy/log-loss minimization as the objective. A fixed grid of candidate values was employed: 1, 5, 10, 100, 250, 500, 1000. The optimal value for the smoker model was 10 samples, and the optimal value for the non-smoker model was 100 samples. This tuning procedure improved cross-entropy by almost an order of magnitude over the default setting of 1 for random forest.

Figure 4:
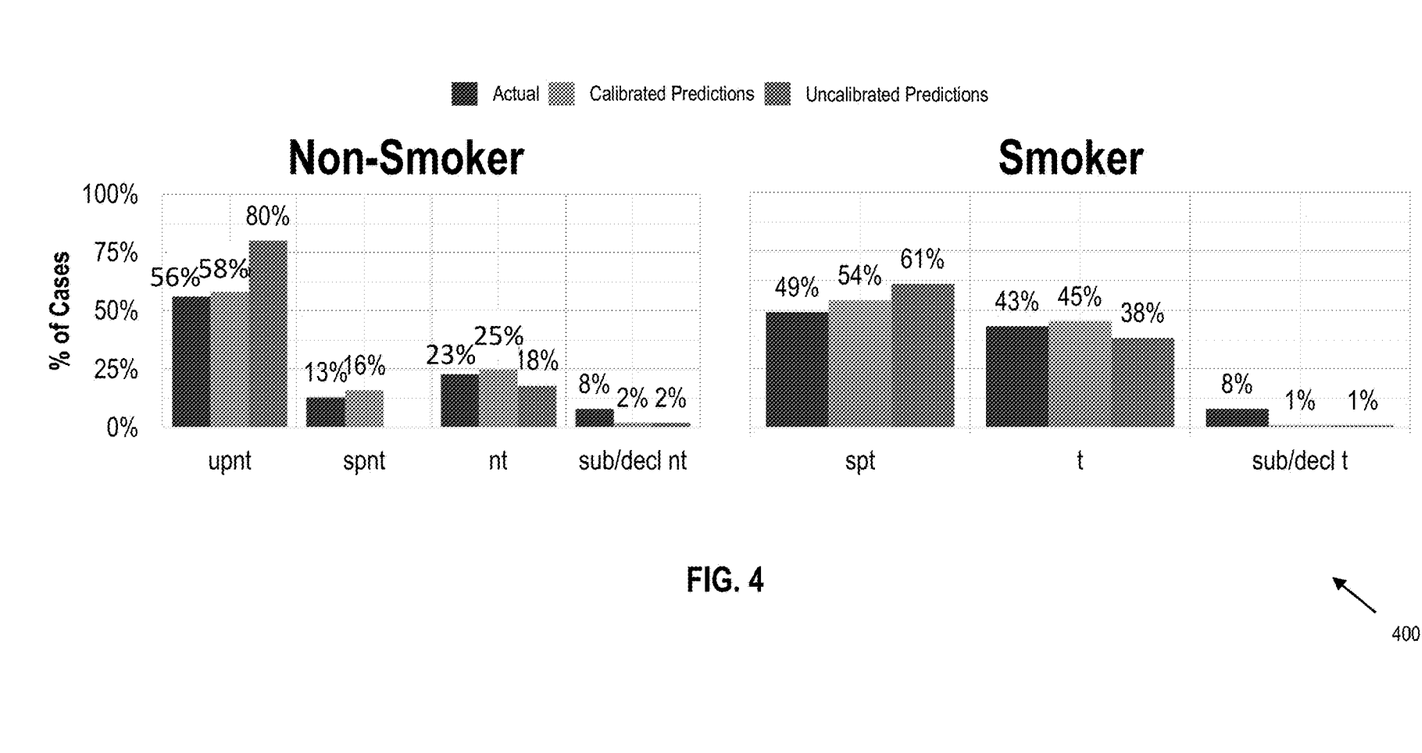
FIG. 4 shows results of calibrating class weights to align marginal risk class distributions, according to an embodiment.

Model predictions were calibrated to ensure that the rate of assigning each risk class would be aligned to historical offers. Since offer rates are not balanced—for instance SPNT ratings are less common than UPNT—model estimates of the most likely class are not naturally well-calibrated. To align model quotes to historical offer rates, model development optimized class weights with model/historical alignment as the objective. Having fixed the complexity parameters, model development tuned class weights for SPNT, NT, and T, holding weights for other classes at 1. This calibration was performed with Bayesian optimization using the objective function $\ell$ defined as follows:

$M_{w,r}$: Rate with which model fit with class weights w assigns class r $A_r$: Rate with class r is assigned in history $l(w) = \|M_w - A\|_2$ As before, the objective function was evaluated with five-fold cross validation. Model development included 30 optimization trials, using Gaussian Process expected improvement as the metric to select the most promising w after each trial. This calibration yielded substantially improved alignment in the risk class spread, shown in FIG. 4. FIG. 4 shows results of tuning class weights to align marginal risk class distributions. Without calibration, SPNT is never selected as the most likely class, UPNT rates are greatly exaggerated, and SPT is somewhat overstated. After calibration, class marginals are aligned with historical offers. One exception is that substandard ratings and declines remain under-predicted. While this calibration process increased cross-entropy by 13%, this cost was accepted to ensure fidelity to historical offer rates. The optimized class weights were 3.4 for SPNT, 2.5 for NT, and 1.2 for T.

FIG. 5 is an example of an individualized underwriting estimate 500. Graphical display 510 depicts risk ratings, highlighting the most likely rating Select Preferred. Text explanation 520 states that the applicant's most likely rating is "Select Preferred" with comments on modeling reasons for this underwriting estimate.

FIG. 6 is an example of a cohort-level estimate 600. Graphical display 610 of risk ratings depicts no assignment of an individual risk rating to the applicant. Text explanation 620 states that male non-smokers aged 32-36 tend to be rated as shown in the display, thereby routing the applicant to an underwriter of the sponsoring enterprise for a more individualized quote.

In various embodiments, the system and method of the present disclosure use additive feature attribution to provide subject-level explanations in the form of input attributions. Additive feature attribution is a technique used to approximate the output of a complicated multivariate function as a linear one on a binary feature space. By building a model in this binary space, the linear coefficients represent the effect of the "presence" or "absence" of a feature on the model's output. For instance, in natural language processing applications, this binary feature is often defined to be the presence or absence of a word.

In the general case, given a data instance $x = \{x_1, x_2, \ldots, x_d\}$ and a model f, this technique employs an interpretable function $h_x: \{0,1\}^d \to \mathbb{R}^d$ that maps a binary vector to the original feature space via the formula $h_x(\{1, 1, \ldots 1\}) = x$. A common choice for $h_x$ is to define this invertible function so that $h_x^{-1}(x')_i = 1$ when $x'_i = x_i$ and $h_x^{-1}$ $(x')_i=0$ otherwise. In this way, given a new data instance x', the ith "interpretable feature" $z'_i=h_x^{-1}(x')t$ can be considered the Boolean answer to the question "Is $x'_i$ equal to x." ?

An additive explanation model $$g: \{0, 1\}^d \to \mathbb{R}, \ g(z) = \varnothing_0 + \sum_{i=1}^{d} \varnothing_i z_i$$

attempts to approximate $g(h_x^{-1}(x')) \approx f(x)$ when $x' \approx x$. As a result, an effect $\varnothing_i$ is attributed to each feature $x_i$, and summing the effects of all feature attributions approximates the output on x:

$$f(x) \approx g(h_x^{-1}(x)) = g(\{1, 1, \ldots 1\}) = \varnothing_0 + \sum_{i=1}^{d} \phi_1$$

In various embodiments, the system and method of the present disclosure employed SHAP values, a feature attribution method that draws on game theory. Scott M. Lundberg, Su-In Lee, "A unified approach to interpreting model predictions," NIPS' 17 Proceedings of the 31st International Conference on Neural Information Processing Systems, Pages 4768-4777; Dec. 4-9, 2017. SHAP values (SHapley Additive exPlanation) is based on Shapley values, a technique used in game theory to determine how much each player in a collaborative game has contributed to its success. Given a cooperative game in which different sets S of players can collaborate and produce certain outcomes V(S), Shapley values provide a method to divide the value generated by the coalition among the different players. The SHAP value framework extends this solution to the problem of dividing the model outcome f(x) between different interpretable features.

In SHAP values, the marginal contribution of a certain feature represents how much the "presence" of that feature changes the outcome of the function, given the "presence" of certain other features. In an example, S represented a subset of the features $\{1, 2, \ldots d\}$ and $z_s$ represented the binary vector where $z_i=1$ for $i \in S$. The marginal contribution $\varnothing_j^s$ for $j \in S$ was defined as the difference in f when the jth feature in z is switched to a 1:

$$\varnothing_j^s = f(h_x(z_{suj})) - f(h_x(z_s))$$

The SHAP value for a certain feature was then defined as a weighted average of all of its marginal contributions:

$$\phi_i = \sum_S \frac{|S|!(d-|S|-1)!}{d!} \phi_i^S$$

This weight represents the number of times the set S can appear as the first |S| features in the set of all possible orderings of the features.

As a method for generating intuitive explanations of underwriting estimator model outputs, SHAP values feature attribution offers the advantage of satisfying three desirable properties for interpretability. First, this technique exactly approximates the function it is explaining: $f(x)=g(h_x^{-1}(x))$. Second, if a variable $x_i$ is missing or unknown, its contribution $\varnothing_i$ is 0. Third, for two models f and f', if $\varnothing_j^s(f) \geq \varnothing_i^s(f')$ for all subsets S, then $\varnothing_i(f)$ is greater for f than for f'.

Disclosed embodiments apply additive feature attribution to interpretability of underwriting estimator outcomes. Because the underwriting estimator is a multi-class model, SHAP yields attributions per-class and per-input. For example, as applied to an underwriting estimator model output that displays the most likely class prediction in the user interface, additive feature attribution may consider only the SHAP attributions corresponding to that class.

An example additive feature attribution is shown in Table 2. Table 2 shows a SHAP attribution for a UPNT model estimate. Positive attribution values support the UPNT rating, while negative attribution values skew the results away from UPNT. In various embodiments, SHAP attributions model explanations may present a small number of top-contributing factors to the user. These top-contributing factors may be presented with or without specific attribution values. These attributions can be presented alongside risk class estimates to improve transparency.

TABLE 2

Example SHAP Attribution for a case UPNT model estimate

| Feature | Value | Attribution |
| --- | --- | --- |
| BMI | 23 | 11.7 |
| Blood pressure | Normal | 7.2 |
| Cholesterol | Good | 2.5 |
| Diabetes | No | 1.16 |
| Asthma | No | 0.18 |
| Smoking 13-24 mo | No | 0.01 |
| Hypothyroidism | No | −0.14 |
| Gender | Male | −1.39 |
| Age | 55 | −9.28 |

In an example, the machine learning underwriting estimator methods of the present disclosure employed the R SHAP package in implementations of SHAP values feature attribution. Correctness tests showed that a sampling-based algorithm implemented by Lundberg and Lee in the Python object-oriented programming language, https://www.python.org, correctly recovered SHAP values in the simple case of linear regression predictive modeling.

In an example, performance tests divided the dataset 220 into 80% training data and 20% test data using random sampling. Models were built and hyperparameters were tuned using the training data, leaving test data for unbiased performance evaluation. Performance testing calculated several metrics on the test set:

Cross-Entropy (log loss or negative log likelihood): This metric provided a cohesive summary of the classifier's probability estimates.

AUC (area under the ROC curve). AUC was calculated on a per-class basis. This yielded seven AUC values in total, each indicating the ability of the model to discriminate a given target class from all other classes.

Accuracy (frequency with which the most likely model-estimated class matches the actual class). This metric was compared with the accuracy of applied-for risk class, an agent-entered quote.

Majority Class: Naive baseline model that always predicts the majority class (UPNT for non-smokers, SPT for smokers).

Relative Mortality: Each risk class is associated with a numeric factor which characterizes anticipated mortality experience for that class. These factors can be used to define a distance between the most likely risk class and the final risk class. The test procedure calculated two metrics using this distance: Mean absolute error (mean of absolute differences in mortality factors); and Bias (sum of signed differences in mortality factors (most likely class factor—actual class factor).

Results of these performance tests showed that the system significantly outperforms conventional "applied-for" quotes entered by agents.

While various aspects and embodiments have been disclosed, other aspects and embodiments are contemplated. The various aspects and embodiments disclosed are for purposes of illustration and are not intended to be limiting, with the true scope and spirit being indicated by the following claims.

The foregoing method descriptions and the interface configuration are provided merely as illustrative examples and are not intended to require, or imply, that the steps of the various embodiments must be performed in the order presented. As will be appreciated by one of skill in the art, the steps in the foregoing embodiments may be performed in any order. Words such as "then," "next," etc., are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code, with it being understood that software and control hardware can be designed to implement the systems and methods based on the description here.

When implemented in software, the functions may be stored as one or more instructions or codes on a non-transitory computer-readable or processor-readable storage medium. The steps of a method or algorithm disclosed here may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

What is claimed is:

1. A method comprising:
   executing, by a server, a predictive machine learning model configured to determine a risk rank representative of a mortality or morbidity risk for an input of risk factor data for an electronic application for an underwriting estimate;
   training, by the server, the predictive machine learning model by inputting into the predictive machine learning model a plurality of historical application details records and a plurality of historical underwriting decision records, wherein model training of the predictive machine learning model develops distributions of refined input values of the input of risk factor data;
   classifying, by the server, the electronic application for the underwriting estimate into one of a first risk group and a second risk group based upon the risk rank determined by the predictive machine learning model;
   determining an attribution value for each of a plurality of factors of the input of risk factor data indicating an effect the factor had on the predictive machine learning model's determination of the risk rank for the input of risk factor data:
   when the electronic application is classified into the first risk group,
      generating, by the server, an individualized underwriting estimate file for the electronic application and a first explanation file including interpretability data, the interpretability data including at least one top-contributing factor selected based on the at least one top-contributing factor having a highest associated attribution value of the attribution values for the plurality of factors evaluated by the predictive machine learning model to predict the risk rank, for display by a user device of information representative of the individualized underwriting estimate file and the first explanation file, wherein the at least one top-contributing factor and the associated attribution value are based on a feature-importance metric; and
   presenting, by the server, for display on the user device, the first explanation file in natural language text, wherein the natural language text indicates the effect of
the at least one top-contributing factor on the predictive machine learning model's determination of
the risk rank for the input of risk factor data based on
the attribution value of the top-contributing factor;
and
when the electronic application is classified into the
second risk group,
generating, by the server, a cohort-level distributions
file for the electronic application and a second explanation file including interpretability data, the interpretability data including the at least one top-contributing factor selected based on the at least one
top-contributing factor having the highest associated
attribution value evaluated by the predictive machine
learning model to predict the risk rank, for display by
the user device of information representative of the
cohort-level distributions file and the second explanation file, wherein the at least one top-contributing
factor and the associated attribution value are based
on a feature-importance metric; and
presenting, by the server, for display on the user device,
the second explanation file in natural language text,
wherein the natural language text indicates the effect of
the at least one top-contributing factor on the predictive machine learning model's determination of
the risk rank for the input of risk factor data based on
the attribution value of the top-contributing factor.

2. The method of claim 1, wherein the predictive machine learning model is executed using the input of risk factor data in response to determining an absence of screening impairment data.

3. The method of claim 1, wherein the input of risk factor data comprises a two-level hierarchy comprised of a level of medical categories and a sub-level of medical categories.

4. The method of claim 1, wherein the first explanation file quantifies contributions to the individualized underwriting estimate file based on the input of risk factor data.

5. The method of claim 1, wherein the second explanation file quantifies contributions to the cohort-level distributions file based on the input of risk factor data.

6. The method of claim 1, wherein the server executes an additive feature attribution algorithm to generate at least one of the first explanation file and the second explanation file, wherein the additive feature attribution algorithm is configured to generate attributions per-class and attributions per-input.

7. The method of claim 1, wherein the server executes a SHAP values (SHapley Additive exPlanation) algorithm to generate at least one of the first explanation file and the second explanation file.

8. The method of claim 1, wherein the server generates rule-based natural language explanations to generate at least one of the first explanation file and the second explanation file.

9. The method of claim 1, wherein model training of the predictive machine learning model developed distributions of refined input values of the input of risk factor data, and applied these distributions of refined input values to marginalize over any case in which model inputs include only coarse input values.

10. The method of claim 1, further comprising:
in response to classifying the electronic application into the second risk group, routing, by the server, the electronic application to an electronic device associated with an underwriter.

11. A system comprising:
an analytical engine server containing a processor configured to execute a plurality of non-transitory computer-readable instructions configured to:
execute a predictive machine learning model configured to determine a risk rank representative of a mortality or morbidity risk for an input of risk factor data for an electronic application for an underwriting estimate;
train the predictive machine learning model by inputting into the predictive machine learning model a plurality of historical application details records and a plurality of historical underwriting decision records;
classify the electronic application for the underwriting estimate into one of a first risk group and a second risk group based upon the risk rank determined by the predictive machine learning model;
determine an attribution value for each of a plurality of factors of the input of risk factor data indicating an effect the factor had on the predictive machine learning model's determination of the risk rank for the input of risk factor data;
when the electronic application is classified into the first risk group,
generate an individualized underwriting estimate file for the electronic application and a first explanation file including interpretability data, the interpretability data including at least one top-contributing factor selected based on the at least one top-contributing factor having a highest associated attribution value evaluated by the predictive machine learning model to predict the risk rank, for display by a user device of information representative of the individualized underwriting estimate file and the first explanation file, wherein the at least one top-contributing factor and the associated attribution value are based on a feature-importance metric; and
presenting for display on the user device, the first explanation file in natural language text,
wherein the natural language text indicates the effect of the at least one top-contributing factor on the predictive machine learning model's determination of the risk rank for the input of risk factor data based on the attribution value of the top-contributing factor; and
when the electronic application is classified into the second risk group,
generate a cohort-level distributions file for the electronic application and a second explanation file including interpretability data, the interpretability data including at least one top-contributing factor and associated attribution value evaluated by the predictive machine learning model to predict the risk rank, for display by the user device of information representative of the cohort-level distributions file and the second explanation file, wherein the at least one top-contributing factor and associated attribution value are based on a feature-importance metric,
wherein the predictive machine learning model comprises a multiclass classification model that executes an additive feature attribution algorithm to generate at least one of the first explanation file and the second explanation file, wherein the additive feature attribution algorithm is configured to generate attributions per-class and attributions per-input; and presenting for display on the user device, the second explanation file in natural language text,
wherein the natural language text indicates the effect of the at least one top-contributing factor on the predictive machine learning model's determination of the risk rank for the input of risk factor data based on the attribution value of the top-contributing factor.

12. The system of claim 11, wherein the predictive machine learning model is executed using the input of risk factor data in response to determining an absence of screening impairment data.

13. The system of claim 11, wherein the first explanation file quantifies contributions to the individualized underwriting estimate file based on the input of risk factor data.

14. The system of claim 11, wherein the second explanation file quantifies contributions to the cohort-level distributions file based on the input for of risk factor data.

15. The system of claim 11, further comprising a non-transitory computer-readable instruction to execute a SHAP values (SHapley Additive exPlanation) algorithm to generate at least one of the first explanation file and the second explanation file.

16. The system of claim 11, wherein the predictive machine learning model applies a random forest models ensemble comprising a smoker model and a non-smoker model.

17. The system of claim 11, wherein the input of risk factor data comprises a two-level hierarchy comprised of a level of medical categories and a sub-level of medical categories.

18. A computer storage medium having computer-executable instructions stored thereon that, when executed by one or more processors, cause the one or more processors to perform operations comprising:
executing a predictive machine learning model configured to determine a risk rank representative of a mortality or morbidity risk for an input of risk factor data for an electronic application for an underwriting estimate,
train the predictive machine learning model by inputting into the predictive machine learning model a plurality of historical application details records and a plurality of historical underwriting decision records, wherein model training of the predictive machine learning model develops distributions of refined input values of the input of risk factor data;
classifying the electronic application for the underwriting estimate into one of a first risk group and a second risk group based upon the risk rank determined by the predictive machine learning model;
determining an attribution value for each of a plurality of factors of the input of risk factor data indicating an effect the factor had on the predictive machine learning model's determination of the risk rank for the input of risk factor data;
when the electronic application is classified into the first risk group,
generating an individualized underwriting estimate file for the electronic application and a first explanation file including interpretability data, the interpretability data including at least one top-contributing factor and associated attribution value evaluated by the predictive machine learning model to predict the risk, for display by a user device of information representative of the individualized underwriting estimate file and the first explanation file, wherein the at least one top-contributing factor and associated attribution value are based on a feature-importance metric; and
presenting for display on the user device, the first explanation file in natural language text,
wherein the natural language text indicates the effect of the at least one top-contributing factor on the predictive machine learning model's determination of the risk rank for the input of risk factor data based on the attribution value of the top-contributing factor; and
when the electronic application is classified into the second risk group,
generating a cohort-level distributions file for the electronic application and a second explanation file including interpretability data, the interpretability data including at least one top-contributing factor selected based on the at least one top-contributing factor having a highest associated attribution value evaluated by the predictive machine learning model to predict the risk rank, for display by the user device of information representative of the cohort-level distributions file and the second explanation file, wherein the at least one top-contributing factor and the associated attribution value are based on a feature-importance metric; and
presenting for display on the user device, the second explanation file in a second natural language text,
wherein the natural language text indicates the effect of the at least one top-contributing factor on the predictive machine learning model's determination of the risk rank for the input of risk factor data based on the attribution value of the top-contributing factor.

19. The computer storage medium of claim 18, wherein the first explanation file quantifies contributions to the individualized underwriting estimate file based on the input of risk factor data.

20. The computer storage medium of claim 18, wherein the second explanation file quantifies contributions to the cohort-level distributions file based on the input of risk factor data.

21. The computer storage medium of claim 18, wherein model training of the predictive machine learning model applied the distributions of refined input values of the input of risk factor data to marginalize over any case in which model inputs include only coarse input values.

* * * * *